United States Patent [19]

Savini

[11] 4,219,685

[45] Aug. 26, 1980

[54] IMPROVING ODOR OF ISOPROPANOL

[75] Inventor: Charles Savini, Warren, N.J.

[73] Assignee: Exxon Research & Engineering Co., Florham Park, N.J.

[21] Appl. No.: 31,761

[22] Filed: Apr. 20, 1979

Related U.S. Application Data

[63] Continuation-in-part of Ser. No. 908,910, May 24, 1978, abandoned, which is a continuation-in-part of Ser. No. 834,240, Sep. 19, 1977, abandoned.

[51] Int. Cl.$^2$ ............................................. C07C 29/24
[52] U.S. Cl. .................................... 568/917; 568/922
[58] Field of Search .............................. 568/917, 922

[56] References Cited

U.S. PATENT DOCUMENTS

| | | | |
|---|---|---|---|
| 2,584,325 | 2/1952 | Bowen et al. | 568/922 |
| 2,585,816 | 2/1952 | Mertzweiller | 568/922 |
| 2,857,436 | 10/1958 | MacKinder et al. | 568/917 |
| 3,624,165 | 11/1971 | Dehn et al. | 568/922 |
| 3,960,672 | 6/1976 | Ester et al. | 203/37 |
| 3,990,952 | 11/1976 | Katzen et al. | 568/921 |

Primary Examiner—Joseph E. Evans

Attorney, Agent, or Firm—C. Leon Kim; Rebecca Yablonsky

[57] ABSTRACT

Methods for deodorizing lower alcohols such as ethanol and isopropyl alcohol and their oxy derivatives such as ethers and esters are disclosed, including contacting these compounds with a deodorizing contact mass comprising, on a support, metals and/or metal oxides, preferably of the metals of Group IB, VIB and VIII of the Periodic Table, where the metal oxides are at least partially reduced to metal and the deodorizing contact mass has a minimum particle dimension of greater than about 0.254 mm so as to be in a form suitable for use in a fixed bed contacting process. In a preferred embodiment, isopropyl alcohol is deodorized employing such deodorizing contact masses, preferably comprising Group VIII metals such as nickel, iron, cobalt and the like, on a support, so that the contact mass has a surface area less than about 1,500 m$^2$ per gram.

Overall isopropyl alcohol finishing procedures are also disclosed employing such deodorizing methods in combination with extractive distillation procedures to produce a high grade, e.g., 91%, and/or anhydrous grade isopropyl alcohol from a crude isopropyl alcohol stream containing more than about 0.0005 percent water.

15 Claims, 3 Drawing Figures

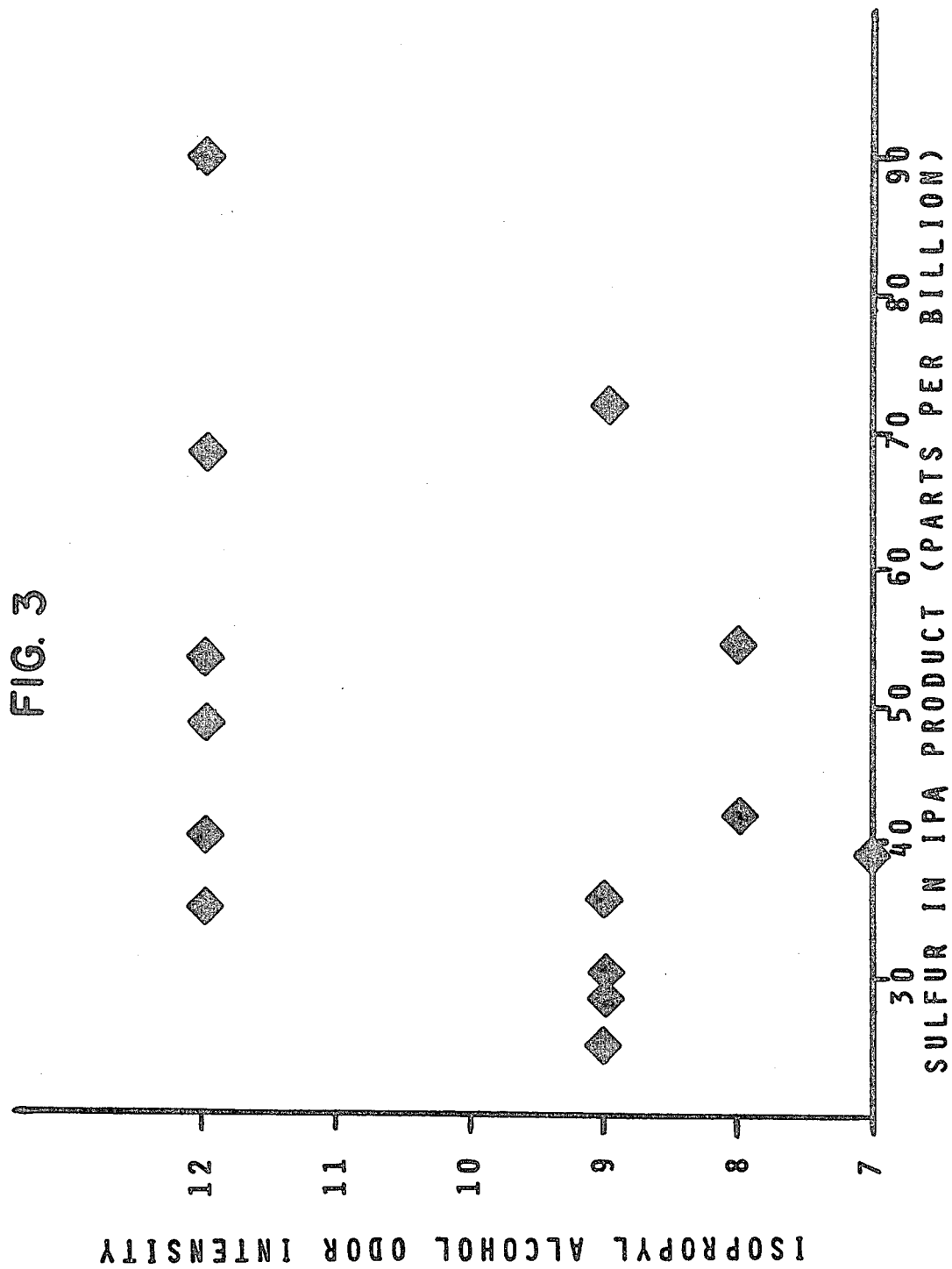

IMPROVING ODOR OF ISOPROPANOL

CROSS-REFERENCE TO RELATED APPLICATIONS

This application is a C.I.P. of Ser. No. 908,910, filed May 24, 1978, now abandoned, which is a C.I.P. of Ser. No. 834,240, filed Sept. 19, 1977, now abandoned.

FIELD OF THE INVENTION

The present invention relates to methods for deodorizing lower alcohols and various oxygenated compounds derived therefrom. Particularly, the present invention relates to methods for deodorizing $C_2$ and $C_3$ alcohols, e.g., ethanol and isopropyl alcohol, and their ether and ester derivatives, e.g., diethyl ether. Still more particularly, the present invention relates to method for deodorizing isopropyl alcohol in connection with commercial isopropyl alcohol finishing processes. The $C_2$-$C_3$ alcohols are customarily manufactured industrially by various methods of dehydration.

BACKGROUND OF THE INVENTION

The production and sale of various oxygenated compounds, such as ethers and in particular lower alcohols such as ethanol and isopropyl alcohol has been hindered by the presence of highly undesirable odors in the commercial products presently being produced. These undesirable odors have been found to be particularly intense and to have caused considerable difficulty in the marketing of these products, which presently have a wide variety of commercial uses. In particular, these commercial uses have included use as solvents, disinfectants, spray products, and in many areas where the presence of such odors is of extreme significance, particularly is cosmetics and medicinal formulations.

This problem is particularly significant with respect to the commercial production of isopropyl alcohol, which in view of its excellent solubility, low toxicity, and cost, has become widely used in such areas as cosmetic products, disinfectants, etc. There has thus been considerable need for commercial processes to deodorize these types of products without unnecessarily hindering the commercial production thereof. These efforts have generally been centered upon processes such as extractive distillation processes, use of ion exchange resins, adsorption on compounds such as activated charcoal, activated alumina, sand, and the like. In many of these cases the patentees have attempted to analyze the various possible causes of negative odor characteristics in these materials, such as in U.S. Pat. No. 2,729,682, assigned to the assignee of the present invention. In the latter patent, however, the patentee attempts to overcome the problems of "recycle" odor by incorporating into the propylene stream a $C_4$ to $C_6$ mono-olefin, followed by water extractive distillation.

In addition, U.S. Pat. No. 2,857,436 teaches the odor improvement of lower alcohols with successive passage of these materials through two different contact masses, a bed of unglazed porcelain and a bed of iron metal such as steel wool, so that the process is inherently uneconomic. The patentee also teaches that other metals such as copper, nickel and zinc have no effect.

None of these prior methods have, however, resulted in a commercially acceptable method for arriving at products having acceptable odor levels with economically and commercially acceptable utility.

Thus, for example, U.S. Pat. No. 2,356,689 teaches a method for the purification of such alcohols employing solid cuprous chloride in specified amounts to stabilize and improve the odor of these alcohols. This method is directed towards the removal of certain small quantities of odor causing impurities therefrom. In addition, this method employs the cuprous chloride as part of the alcohol finishing or purification procedure.

Furthermore, U.S. Pat. No. 2,663,745 discloses a process whereby the quality of various alcohols is improved by intimate contact with small sized glass particles, i.e., having particle sizes of between about 4 and 20 mesh.

In another area, not concerned with alcohols made by hydration methods but rather with oxo alcohols of higher molecular weight, $C_4$-$C_{12}$, made by the hydroformylation of olefins followed by hydrogenation with sulfided catalysts, the patentee in U.S. Pat. No. 2,585,816 discloses the treatment of alcohols such as isooctanol of high sulfur content by metals such as mercury, copper and nickel, viz., Raney nickel or nickel on a support, essentially for reducing the sulfur content thereof, e.g. from 58-83 ppm to 10-27 ppm, thereby improving color. However, such treatment is not capable of deodorizing isooctanol to produce a pleasant smelling product, as demonstrated in Example 8 below.

In a more recent development, Japanese Pat. No. 51-1684 discloses another method for purifying isopropyl alcohol comprising contacting the alcohol with various Raney metals, including Raney nickel. This method includes contacting with the Raney metal, preferably in the presence of a reducing gas such as hydrogen. The Raney metals are present in amounts of from about 0.01 to 5 parts per hundred parts of alcohol. This procedure is not commercially feasible, however, particularly due to the fact that the Raney metals are extremely unstable and potentially dangerous to use.

The removal of odor from lower alcohols is difficult, inasmuch as the contaminants responsible are present in very small amounts and one doesn't know just which contaminants are causing the odor. Although the references cited date back to the early 50's, the problem of deodorizing isopropanol has persisted up to present times. Thus, the problem is a difficult one, the solution to which has a high degree of unpredictability so that this is an area where there is little obviousness.

The search has therefore continued for new methods for deodorizing lower alcohols, i.e.. $C_2$ and $C_3$ alcohols, such as isopropyl alcohol, and their ether and ester derivatives such as diethyl ether in a commercially acceptable and simple manner.

SUMMARY OF THE INVENTION

It has now been unexpectedly discovered that said lower alcohols and their oxygenated compounds can be deodorized to a highly sufficient extent in a simple, highly economical, and highly adaptable manner by contacting these compounds with a deodorizing contact mass comprising a metal and/or a metal oxide which is at least partially reduced to metal and where the deodorizing contact mass has a suitable dimension, e.g., a minimum particle dimension of greater than about one-hundredth of an inch (1/100"), so that it can be effectively employed in a fixed bed contacting process. That is, these particle sizes permit the deodorizing contact mass to be used in a column and to support itself sufficiently therein to be useful in such fixed bed contacting processes.

It is therefore necessary that the deodorizing contact mass have such a minimum particle dimension of greater than about 0.254 mm (1/100 inches), but preferably a minimum particle dimension of greater than about 0.794 mm (1/32 inches), and most preferably less than about 6.352 mm (¼ inches).

In a preferred embodiment, the deodorizing contact mass thus has an effective surface area of less than about 1,500 m² per gram, and most preferably the deodorizing contact mass comprises one or more of the metals or metal oxide compounds discussed above incorporated in a porous support. The supports used will preferably have a surface area of between about 1 and 1,000 m² per gram.

In another embodiment of the present invention, the deodorizing contact mass can comprise either a metal or a metal oxide of the metals of Groups IB, IIB, IVB, VB, VIB, VIIB, and VIII of the Periodic Table, preferably Groups IB, VB, VIB, VIIB, and VIII, and most preferably Groups IB, VIB, and VIII.

In another embodiment of the present invention, it has been further discovered that a highly deodorized commercially acceptable stream of isopropyl alcohol can be produced by contacting a stream of isopropyl alcohol with such deodorizing contact masses. Preferably, an initial stream of isopropyl alcohol containing from about 0.0005 to 90 percent water is contacted with the deodorizing contact masses in a finishing procedure, so that ultimately a deodorized stream of isopropyl alcohol is produced, preferably containing less than about 0.01 percent water.

In a preferred embodiment of this aspect of the present invention, the finishing procedure for preparation of isopropyl alcohol includes various extractive distillation steps, including a first distillation step in a tower maintained at a temperature such that undesirable impurities are removed overhead, and a bottoms stream of isopropyl alcohol is prepared containing from about 60 to 90 percent water. Furthermore, the preferred isopropyl alcohol finishing procedure will also include a second distillation step at a temperature of from about 75° to 150° C., wherein an improved isopropyl alcohol stream containing from 9 to 15 percent water is removed overhead. Finally, it is most highly preferred that this finishing procedure include a third distillation step conducted at a temperature of from about 75° to 150° C., in which the finished isopropyl alcohol stream is removed as bottoms, and it includes from 9 to 15 percent water, while various undesirable lower boiling components are removed overhead therein.

In these preferred finishing procedures for the production of isopropyl alcohol, the contacting step of the present invention with a deodorizing contact mass may be carried out at any stage, but preferably either prior to or subsequent to the third distillation step.

BRIEF DESCRIPTION OF THE DRAWINGS

The following detailed description of the present invention may more readily be understood by reference to the drawings, wherein;

FIG. 3 is a graph showing isopropyl alcohol odor intensity plotted against sulfur therein in parts per billion.

DETAILED DESCRIPTION

Figure 1:
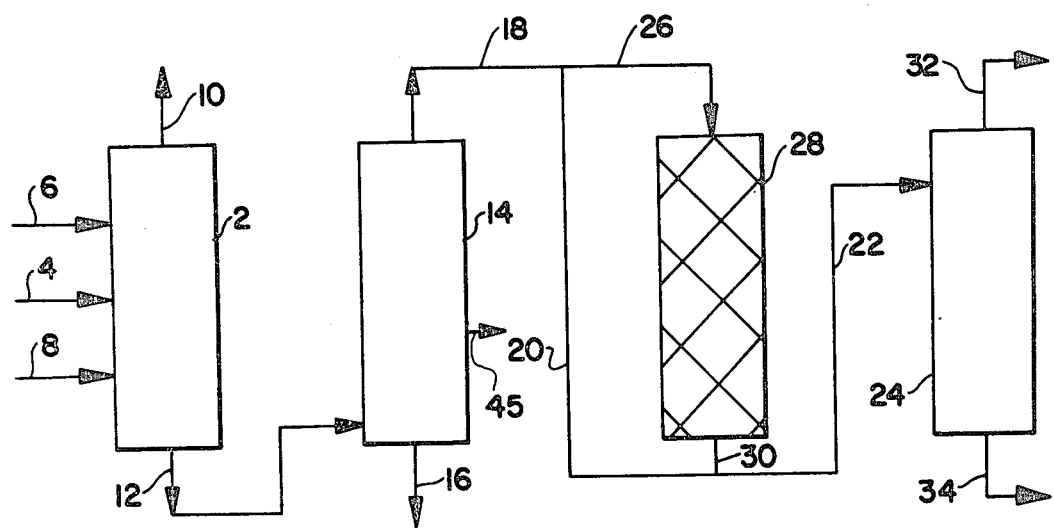
FIG. 1 comprises a schematic diagram of a process scheme for production of isopropyl alcohol incorporating the present invention therein.

One aspect of the significance of the present invention is the fact that it represents a simple, economically desirable, efficient method for incorporation into conventional processing techniques for the production of various oxygenated compounds which will not disrupt the commercial production of these materials, but will lend itself to adaptation to these processes so that final products can be produced having excellent odor properties. In addition, the deodorizing contact mass employed in this invention can be utilized at various conditions, and can be continuously contacted with the stream to be deodorized for extremely long periods of time without the need for regeneration or the like. The contacting procedure utilized is relatively simple, and primarily only results in the deodorizing of the contact stream without any serious side effects, and/or alterations to that stream. Part of this benefit may be the result of the specific mechanism by which such deodorizing occurs; however it is not considered part of the present invention, and indeed is not fully understood at this time. It probably includes, however, either removal of negative characteristics, or the addition of desirable odor characteristics of the materials being so treated, or a combination of these effects.

With particular reference to prior systems such as that of Japanese Pat. No. 51-1684 employing Raney metals for odor improvement of isopropyl alcohol, the present invention demonstrates a number of significant advantages. First, significantly lower yield loss during product purification may be realized due to the far lower selectivity to undesired by-products. Also, higher metal treatment capacities, elimination of metal contaminants in the product without the need for costly filtration and/or distillation techniques, significantly lower residence time, elimination of objectionable waste streams with consequent clear ecological advantages, elimination of the need for adding hydrogen during treatment, and overall lower costs are also associated with this invention.

One of the striking odor characteristics of lower alcohols to be treated in accordance with the instant inventive process resides in the fact that the feed lower alcohols contain relatively small quantities of sulfur-containing impurities, typically below about 100 parts per billion; and also that such sulfur content does not appear to have any direct correlation with its odor.

The deodorizing contact mass which can be employed in the present invention is, of course, the most significant aspect thereof. These deodorizing contact masses must be suitable for use in a fixed bed or fluidized bed contact process. Thus, they must be in a physical condition adaptable for such usage.

In particular, the deodorizing contact mass of the present invention should have the particular minimum particle dimensions discussed above, and furthermore have an effective surface area of less than about 1,500 m² per gram, preferably less than about 1,000 m² per gram, and most preferably between about 1 and 500 m² per gram.

One method of obtaining such deodorizing contact masses having such surface areas is to incorporate the metals or at least partially reduced metal oxides in an effective porous support material. Such incorporation may be accomplished by various techniques known in the art, such as impregnation, ion exchange, simultaneous precipitation, and/or coprecipitation, or by incorporation of suitable surface stabilizing elements into a massive metal/metal oxide structure, or by any other technique which results in highly dispersed metal/metal oxide surfaces. These support materials themselves can be of various types, including silica, alumina, silica/alumina, zeolites, diatomaceous earth, carbon, various clays, refractory oxides, and the like.

In particular, a number of such specific support materials and their surface area and pore volume characteristics are included in Table I below.

TABLE I

| Support Material | Surface Area (m²/gm) | Cum. Pore Volume (cc/gm) |
|---|---|---|
| Porous silica gels | 200–700 | 0.6–0.8 |
| Compounded fused silica | 40–60 | ~0.3 |
| Activated alumina (Alorico) | 175 | ~0.4 |
| Activated gamma-alumina | 220 | ~0.4 |
| Alpha-alumina | 10 | ~0.1 |
| Silica/alumina | 200–700 | 0.2–0.7 |
| Silica/magnesia | 330–630 | 0.3–0.5 |
| Activated carbons | 500–1500 | 0.6–0.8 |
| Activated clays | 150–225 | 0.4–0.5 |
| Kieselguhr (Celite 296) | 4–5 | 1–1.2 |
| Porous porcelain | 1–2 | 0.1–0.2 |

Furthermore, the metal used in connection with the deodorizing contact mass of this invention can be either metals and/or at least partially reduced metal oxides.

In particular, metals and/or metal oxides of Groups IB, IIB, IVB, VB, VIB, VIIB, and VIII of the Periodic Table are utilized, preferably Group IB metals, such as copper, silver and gold, preferably copper, Group IIB metals such as zinc, cadmium, and mercury, preferably zinc, Group VB metals such as vanadium, niobium, and tantalum, preferably vanadium, Group VIB metals, such as chromium, molybdenum, and tungsten, preferably molybdenum, Group VIIB metals, such as manganese and rhenium, preferably manganese, and Group VIII metals, such as nickel, cobalt, palladium, iron, platinum, rhodium, ruthenium, iridium and osmium, most preferably rhodium, nickel, platinum, cobalt, iron, palladium and combinations thereof, i.e., Rh/Ni.

Among the most preferred deodorizing contact masses in accordance with the present invention are certain commercially available hydrogenation catalysts which, however, are employed in the conditions of the present invention and do not act as conventional catalysts in that sense. These include such commercial hydrofining, hydrogenation, dehydrogenation, oxidation, ammonia synthesis and dissociation, reforming, hydrotreating and gas purification catalysts (in reduced or activated form) as those sold commercially by Girdler, W. R. Grace, Calsicat and Engelhard.

The deodorizing contact mass of the present invention will most preferably be employed in a fixed bed contacting tower. The materials will thus be contacted, preferably in a downflow manner, with the feed stream to be deodorized. Such contacting will preferably be carried out at a temperature of between 50° and 300° C., preferably between 60° and 150° C., and most preferably between 60° to 120° C., and at a pressure generally between about 0 and 400 psig, preferably from 0.5 to 250 psig, and most preferably from about 1 to 150 psig. With respect to these conditions, however, as discussed above, conditions can be selected which are the least severe possible, and which are most compatible with the particular process scheme with which the present method is to be employed. Finally, the contacting can be carried out at space velocities of between about 0.2 and 50 v/hr/v, preferably between about 0.5 and 35 v/hr/v, and most preferably between 1 and 24 v/hr/v.

Figure 2:
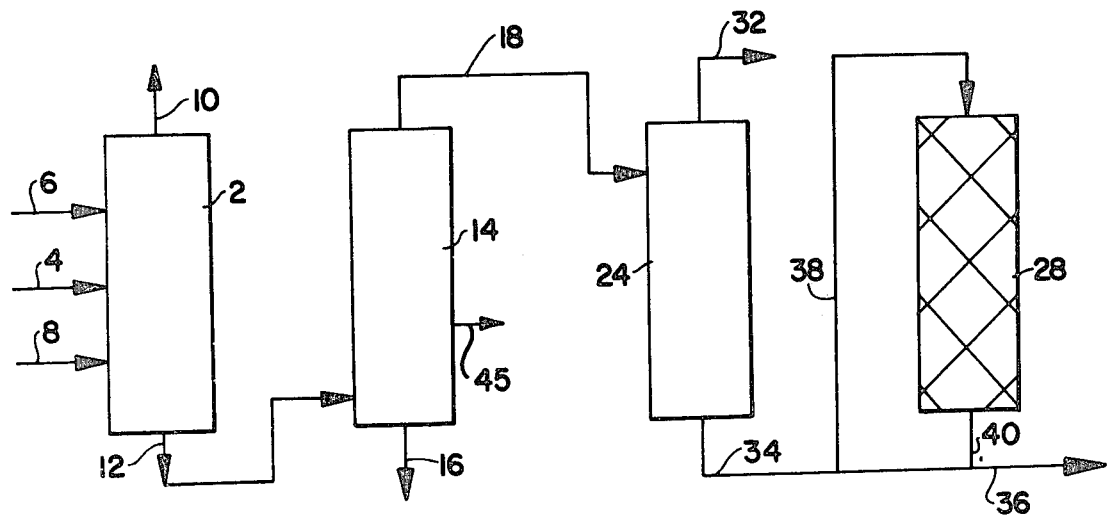
FIG. 2 comprises a schematic diagram of an alternative process scheme for such production of isopropyl alcohol.

The present invention can be more fully understood with reference to FIGS. 1, 2 and 3 hereof. In these figures, the method of the present invention is incorporated into a conventional isopropyl alcohol finishing scheme; and also the odor/sulfur content relation in isopropyl alcohol is illustrated.

With reference to the first two figures herein, wherein like numerals refer to like portions thereof, FIG. 1 represents such an isopropyl alcohol processing and deodorizing scheme.

Thus, referring to FIG. 1, crude feed stream is fed into extractive distillation tower 2 through line 4. This feed stream generally comprises isopropyl alcohol and from about 35 to 55 weight percent water, as well as other impurities, such as isopropyl ether. Water is fed into tower 2 through line 6, and steam through line 8. In tower 2, which is maintained at a temperature of between about 50° and 150° C., preferably from 80° to 130° C., and at a pressure of from 0 to 20 psig, and preferably from 5 to 15 psig, the undesirable impurities and removed overhead through line 10. These impurities include various ethers, as well as other such undesirable components. The thus refined isopropyl alcohol stream, again containing between about 40 to 90 percent water, preferably between about 60 to 90 percent water, is withdrawn as bottoms through line 12 and carried to tower 14 for further distillation. In tower 14, generally referred to as the alcohol tower, the isopropyl alcohol stream is further concentrated by removing water as bottoms through line 16. This is accomplished by maintaining this tower 14 at a temperature of between about 75° and 150° C., preferably of between about 80° and 120° C., and a pressure of between about 0 and 20 psig, preferably of between about 5 and 15 psig. The isopropyl alcohol/water mixture, now containing from about 9 to 15 weight percent water is thus withdrawn overhead through line 18, and heavy impurities are purged through line 45. While the isopropyl alcohol/water mixture could thus, in the conventional manner, be carried by lines 20 and 22 to a further distillation column 24, or as shown in FIG. 2 directly through line 18 to such a tower 24, generally referred to as the acetone tower, wherein any ketones such as acetone can be removed overhead as light ends in accordance with the present invention, line 20 may be closed partially or completely, as desired, by valve means, so that at least part of the isopropyl alcohol solution removed from tower 14 can be carried through line 26 into the deodorizing tower 28 of the present invention. In this tower 28, and fixed bed catalyst discussed above is maintained, so that the isopropyl alcohol/water mixture passes thereover, at the conditions discussed above. The deodorized and substantially improved isopropyl alcohol/water stream thus obtained is withdrawn from tower 28 through line 30 and can then pass through line 22 into acetone tower 24. Acetone tower 24 is thus maintained at a temperature of between about 70° and 120° C., preferably from 75° to 110° C., and at a pressure between about 0 and 20 psig, preferably from 5 to 15 psig. In this manner, the acetone and/or other ketones and lighter impurities contained in the isopropyl alcohol mixture can be withdrawn overhead through line 32, while a prime grade isopropyl alcohol stream is withdrawn from the bottom of tower 24 through line 34. This material generally comprises the azeotrope, including about 91 percent isopropyl alcohol in water. The overheads withdrawn from line 32 including acetone, some isopropyl alcohol, and some water is principally a reject stream from acetone tower 24. The prime grade isopropyl alcohol withdrawn as bottoms through line 34 from tower 24 can be further finished by dehydration process to produce greater than 99 percent isopropyl alcohol therefrom.

With specific reference to FIG. 2, it can be seen that the feed withdrawn overhead from tower 14 through line 18, and again containing isopropyl alcohol containing from about 9 to 15 percent water, is fed directly to acetone tower 24 for further distillation. This tower operates in the manner described above with respect to acetone tower 24 in the scheme of FIG. 1. However, in this case, the deodorizing tower 28 of the present invention is located downstream from tower 24 so that the prime grade isopropyl alcohol product withdrawn from tower 24 through line 34, instead of passing directly out of the process through line 36, can be forwarded through line 38 into tower 28 for contact with the deodorizing mass of the present invention. The deodorized stream can then be withdrawn through line 40 and line 36.

With regard to FIG. 3, it can be seen that a low level of sulfur present in an isopropanol sample does not necessarily mean a lower level of odor detected from the sample. This suggests that the odor-causing impurities present in lower alcohols may be more than simple sulfur compounds; and also that the deodorizing metals or metal oxides employed in the instant invention may serve a different function from that which has been known in the prior art.

While the illustrations of FIGS. 1 and 2 are exemplary of certain embodiments of the present invention, it will be appreciated that the deodorizing tower may be located in many different locations throughout an isopropyl alcohol finishing process, particularly since it is so highly adaptable to various conditions of temperature, pressure, space velocity, stream compositions, etc., and furthermore since it can be used over extended periods of time and not result in the disruption of these process streams.

The present invention may be more fully understood with reference to the following examples thereof.

EXAMPLE 1

Three hundred milliliters of a 91% isopropyl alcohol product having a 12+ RHB odor class (non-saleable, off-specification material) was heat soaked in a 500 milliliter flask with thirty (30) grams of ⅛" tablets of activated ENCAR hydrogenation catalyst having the following characteristics:
Type: Co-precipitated nickel-copper-silica-kieselguhr catalyst
Ni content: 45 wt. %
Cu content: 4.5 wt. %
BET surface area: 250 $m^2$/gm
Apparent bulk density: 53 lb/$ft^3$
Crush strength: 7 lb (⅛"×⅛" tablet)
Cumulative pore volume: ~0.35 cc/gm Contacting at atmospheric pressure and at a temperature of about 78° C. was continued for about 2 hours. The resultant isopropyl alcohol was evaluated by an Odor Panel after treatment. The product was judged to be comparable to cosmetic quality alcohol and to be free from recycle odor. The results are included in Table II below.

EXAMPLE 2

Seventy-two grams of a commercial hydrogenation catalyst sold by Harshaw as Harshaw Ni-0104T-⅛ hydrogenation catalyst having the following characteristics:
Type: Nickel on kieselguhr in ⅛" tablet form
Ni content: 58 wt. %
BET surface area: 160 $m^2$/gm
Apparent bulk density: 90 lb/$ft^3$
Crush strength: 9 lb (⅛"×⅛" tablet)
Cumulative pore volume: ~0.20 cc/gm
was contacted with 300 milliliters of a 91% isopropyl alcohol product having a 12+ RHB odor class in a 500 milliliter flask. The temperature of this system was maintained at about 80° C. for 3 hours at atmospheric pressure. The resultant isopropyl alcohol stream was rated by an Odor Panel, and the results are again included in Table II below. This product was again judged to be of cosmetic quality and free from recycle odor.

EXAMPLE 3

Fifty-six grams of a commercial hydrogenation catalyst sold by Harshaw as Harshaw Ni-3250 T-⅛ hydrogenation catalyst having the following characteristics:
Type: Nickel on support in ⅛" tablet form
Ni content: 52 wt. %
BET Surface area: 145 $m^2$/gm
Apparent bulk density: 68-69 lb/$ft^3$
Crush strength: ~18 lbs. (⅛"×⅛" tablet)
Cumulative pore volume: ~0.32 cc/gm
was heat soaked in 300 milliliters of a 91% isopropyl alcohol product having a 12+ RHB odor class in a 500 milliliter flask for three hours at a temperature of about 80° C. and atmospheric pressure. The resultant isopropyl alcohol stream was rated by an Odor Panel, and the results are again included in Table II below. This product was again judged to be of cosmetic quality and free from recycle odor.

EXAMPLES 4–7

The procedure of Example 3 was duplicated in four successive runs, except that the same Harshaw Ni-3250 T-⅛ hydrogenation catalyst was re-used in each run. In each case the resultant isopropyl alcohol stream was rated by the Odor Panel, and the results are again included in Table II below. These products were again judged to be of cosmetic quality and free from recycle odor, thus demonstrating that reduced catalyst effectiveness during successive product treatments was not observed.

TABLE II

| | Odor Evaluation by Odor Panelists ODOR RATING[1] | | |
|---|---|---|---|
| Example No. | Feed | Product | Product Quality Relative to Cosmetic Grade |
| 1 | 12+RHB | 2 | Equivalent |
| 2 | 12+RHB | 2+ | Comparable, but not as good |
| 3 | 12+RHB | <2 | Equal or better |
| 4–7 | 12+RHB | <2 | Equal or better |
| Cosmetic Grade Isopropyl Alcohol | | 2 | |

TABLE II-continued

Odor Evaluation by Odor Panelists
ODOR RATING[1]

| Example No. | Feed | Product | Product Quality Relative to Cosmetic Grade |
|---|---|---|---|
| (Control) | | | |

[1] Isopropyl alcohol odor class rating scale Lowest Intensity-Odor Class 2 Highest Intensity-Odor Class 12 Suffix indicates odor type, e.g. "R" designates recycle odor, "HB" designates high boiler odor

EXAMPLE 8

Isooctyl Alcohol Treated with Nickel Catalyst

Isooctyl alcohol was produced in a commercial plant by the oxonation of a $C_7$ olefin stream at approximately 3000 psi using carbon monoxide and hydrogen in the presence of a soluble cobalt catalyst. The crude oxo product, consisting primarily of $C_8$ aldehydes, alcohols, and unreacted olefins, was demetalled (i.e., the oxo catalyst was removed) and was then hydrogenated over a 10% $MoS_2$ on charcoal catalyst to give a mixture of predominantly $C_8$ alcohols. After distillation to remove the light ends and some heavy boilers, the isooctyl alcohol was stored for sales.

A sample of the above $C_8$ oxo alcohol was treated with 19 wt. percent of a prereduced 50% nickel catalyst by heat soaking/refluxing the alcohol in the absence of hydrogen for various periods of time as shown in Table I below. The products were rated by an Odor Panel. Results of the study show that (i) isooctyl alcohol treated with a nickel contacting mass did not give a low odor, cosmetic grade alcohol; and (ii) the odor quality of the $C_8$ oxo alcohol was not improved by treating the alcohol with a nickel catalyst contacting mass.

TABLE III

Isooctyl Alcohol Heat Treated with 19 Wt. Percent Nickel Catalyst[1] At Atmospheric Pressure

| Experiment | Odor Rating[2][3] By Panel | Comments of Panel |
|---|---|---|
| A. Base Case-Untreated $C_8$ Oxo Alcohol | Class 12+ Alcohol | Offensive Odor; Not Cosmetic Grade Alcohol |
| B. $C_8$ Oxo Alcohol Heated for 1½ Hours at 138° C. | Class 12+ Alcohol | Offensive Odor; Not Cosmetic Grade Alcohol |
| C. $C_8$ Oxo Alcohol Heated for 3 Hours at 138° C. | Class 12+ Alcohol | Offensive Odor; Not Cosmetic Grade Alcohol |
| D. $C_8$ Oxo Alcohol Heated for 6 Hours at 100° C. | Class 12+ Alcohol | Offensive Odor; Not Cosmetic Grade Alcohol |

NOTES:
[1] Nickel contacting mass was comprised of 50 wt. percent nickel metal supported on a refractory oxide (Harshaw Ni-3250T⅛).
[2] Odor rating based upon an intensity scale ranging from Class 2 Alcohol (very low odor intensity) to Class 12 Alcohol (highest odor intensity on rating scale). Note that 12+ goes beyond and is worse than the highest intensity on the normal rating scale.
[3] Odor panelists could not distinguish between $C_8$ alcohol samples, i.e., no difference was noted between treated versus untreated samples.

Thus it can be concluded that treatment with nickel metal on a support is not capable of deodorizing isooctanol so as to achieve better than a 12+ odor, such representing an obnoxious and highly disagreeable odor. It follows that the deodorization of isopropyl alcohol and of isooctanol are not the same problem.

EXAMPLE 9

In order to compare the present process with that of Japanese Pat. No. 51-1684 the odor improvement of isopropyl alcohol in a post treatment deodorization process was carried out under comparable conditions with a nickel supported contacting mass in accordance with the present invention (a commercial Harshaw Ni-3250T supported nickel hydrogenation catalyst) and with Raney nickel. The results obtained are summarized in Table IV below. In addition to those results, it is also noted that the process of the present invention, as compared to that of the Japanese patent, does not require product filtration or distillation after treatment, raises no catalyst separation or waste stream disposal problem and does not require the use of hydrogen therein.

EXAMPLE 10

A 91% isopropyl alcohol stream having a 12+ RHB odor class was pumped continuously through a two inch diameter pipe filled with commercial Harshaw Ni-3250T hydrogenation catalyst. Flow rates of from about 1 to 24 volumes of the isopropyl alcohol per hour per volume of nickel contacting mass were employed, as well as temperatures of from 55 to 85° C., and pressures from atmospheric to about 250 psig. The treated isopropyl alcohol product was markedly improved in odor quality, from a bad odor feed to a product similar to cosmetic grade. The product furthermore did not contain measureable amounts of residual metals, and the bed was still effective after more than 10,000 volumes of isopropyl alcohol per volume of nickel contacting mass had been processed therein.

TABLE IV

| Property | Raney Nickel | Harshaw Ni-3250T Supported Nickel |
|---|---|---|
| (A) Product Clarity After Post Treatment | Turbid | Water white (no particulates) |
| (B) Residual Metal | | |
| (i) in decanted product | 45 ppm Al and 48 ppm Ni | None detected (i.e. <25 ppb) |
| (ii) in filtered product | 17 ppm Al and 2 ppm Ni (thru a 10 micron filter) | None detected (thru a 20 micron filter) |
| (C) Yield Loss (i.e. % By-Product Formed) | | |
| (i) 60° C./1 hour contact time/ 100 parts isopropyl alcohol and 5 parts metal contacting mass | 0.3% | <0.1% |
| (ii) 80° C./1 hour contact time/100 parts isopropyl | | |

TABLE IV-continued

| Property | Raney Nickel | Harshaw Ni-3250T Supported Nickel |
|---|---|---|
| alcohol and 5 parts metal contacting mass | 1.2% | 0.1% |
| (D) Metal Contacting Mass Capacity (i.e. parts isopropyl alcohol deodorized per parts metal contacting mass) | 333 max (from Japanese patent) | >10,000 |
| (E) Minimum Contact Time for Odor Improvement | 1 hour (from Japanese patent) | <10 minutes |

EXAMPLES 11-17

About 300 milliliters of a 91% isopropyl alcohol having a 12+ RHB odor class was treated in a 500 milliliter flask for about 3 hours at a temperature of about 80° C. under atmospheric pressure by employing about 15 grams of a series of different deodorizing metals described in Table V below. The resultant isopropyl alcohol stream was rated by an Odor Panel and judged to be free of recycle type odor and suitable for odor sensitive end uses.

TABLE V
APPLICABILITY OF VARIOUS METALS AS DEODORIZING AGENT FOR ISOPROPANOL

| Example No. | Deodorizing Agent |
|---|---|
| 11 | 0.5% Pt/Al$_2$O$_3$ |
| 12 | 0.5% Rh/Al$_2$O$_3$ |
| 13 | 0.5% Ru/Al$_2$O$_3$ |
| 14 | 0.5% Pd/Al$_2$O$_3$ |
| 15 | 10% Fe/1% Cu/Al$_2$O$_3$ |
| 16 | 50% Co/Refractory Oxide Support |
| 17 | 6% Ni/19% W/Al$_2$O$_3$ |

EXAMPLE 18A

A 91% isopropyl alcohol stream having a 12+ RHB odor class was pumped through a ½" tube filled with 25 cc of Ni-3250T-⅛ catalyst at a space velocity of 4.0 v/hr/v and at atmospheric pressure and a temperature of about 80° C. The treated isopropyl alcohol was judged by an Odor Panel to be markedly improved in odor quality with all objectionable type odors being removed and to be suitable for low odor type alcohol end uses.

EXAMPLE 18B

The same 91% isopropyl alcohol stream of 12+ RHB odor class was pumped through a ½" tube filled with equal volumes of Ni-3250T-⅛ catalyst and 0.5% Rh/Al$_2$O$_3$ T-⅛ catalyst placed in the reactor tube such that the nickel catalyst contacted the alcohol before the rhodium catalyst. The odor treatment conditions employed were identical to those used in Example 18A. The product alcohol was judged by the Odor Panel to be of odor quality superior to the purified alcohol produced in Example 18A.

EXAMPLE 19

A series of untreated isopropanol samples were first analyzed by employing a Houston Atlas Sulfur Analyzer marketed by Houston Atlas, Inc. in order to determine their sulfur content; and then subsequently were subjected to odor evaluation by an Odor Panel for the purpose of determining whether or not there exists a functional relationship between the sulfur content and the level of objectionable odor detected in the isopropanol samples. The results are plotted in FIG. 3; it was concluded that there does not exist a direct relationship between the two.

The foregoing description of the invention and specific embodiments are for the purposes of illustration only, and not for limitation of the invention. It is to be understood that the invention is not to be limited by any theory or illustration presented, but only by the following claims.

What is claimed is:

1. A method for deodorizing isopropyl alcohol wherein isopropyl alcohol is contacted with a deodorizing contact mass consisting essentially of metals or metal oxides incorporated in a porous support wherein said metal oxides are at least partially reduced to metal, said metals and oxides of the metals being selected from the group consisting of Groups IB, VIB and VIII of the Periodic Table and mixtures thereof and said support being selected from the group consisting of Kieselguhr, silica, alumina, silica/alumina, carbon, clay zeolites, refractory oxides, and mixtures thereof, and wherein said deodorizing contact mass has a minimum particle dimension of greater than about 0.01 inch so as to be in a form suitable for use in a fixed bed contacting process.

2. The method of claim 1 wherein said deodorizing contact mass has an effective surface area of less than about 1,500 m$^2$/gram.

3. The method of claim 1 wherein said porous support has an effective surface area of between about 1 and 1,000 m$^2$/gram.

4. The method of claim 1 wherein said metal is selected from the group consisting of nickel, cobalt, iron, palladium, rhodium, ruthenium, platinum, iridium, osmium, tungsten, copper and mixtures thereof.

5. The method of claim 1 wherein the isopropyl alcohol is a stream of isopropyl alcohol and water.

6. The method of claim 5 wherein metals used are selected from Group VIII of the Periodic Table.

7. The method of claim 5 wherein said stream of isopropyl alcohol includes from about 0.0005 to 90 weight percent water.

8. The method of claim 5 wherein said deodorizing contact mass has an effective surface area of less than about 1,000 m$^2$/gram.

9. The method of claim 5 including distilling said stream of isopropyl alcohol in a first tower at a temperature of between about 80° and 130° C., and a pressure of between about 5 and 15 psig, so as to produce a liquid stream of isopropyl alcohol from the bottom of said first tower, containing between about 40 and 90 weight percent water, and to produce an overhead vapor stream from said first tower containing undesirable impurities.

10. The method of claim 9 including distilling said liquid stream of isopropyl alcohol containing between about 40 and 90 weight percent water in a second tower at a temperature of between about 80° and 120° C., and a pressure of from about 5 to 15 psig, so as to produce a highly concentrated liquid stream of isopropyl alcohol from the top of said second tower, said stream containing between about 9 and 15 percent water, a bottom stream from said tower comprising water, and a side stream from said tower comprising heavy impurities.

11. The method of claim 10 including condensing an overhead vapor stream comprising isopropyl alcohol from said second tower, to produce said stream containing between about 9 and 15 percent water, and distilling said isopropyl alcohol stream in a third tower maintained at a temperature of between about 75° and 110° C., and a pressure between about 5 and 15 psig, so as to remove a highly purified isopropyl alcohol stream in a liquid state from the bottom of said third tower, said stream containing between about 9 and 15 percent water, and an overhead vapor stream from said third tower comprising light impurities.

12. The method of claim 11 wherein said contacting with said deodorizing contact mass is carried out utilizing said overhead stream of isopropyl alcohol withdrawn from said second tower.

13. The method of claim 11 wherein said contacting with said deodorizing contact mass is carried out with said liquid stream of isopropyl alcohol withdrawn from the bottom of said third tower.

14. The method of claim 7 wherein said stream of isopropyl alcohol comprises the product stream from an alcohol dehydration process.

15. The method of claim 5 wherein metals used are selected from the group consisting of nickel, cobalt, iron, palladium, rhodium, ruthenium, platinum, copper, tungsten, and mixtures thereof.

* * * * *